United States Patent [19]

Burns

[11] Patent Number: 5,435,997
[45] Date of Patent: Jul. 25, 1995

[54] **TOPICAL AGENT AND METHOD FOR THE TREATMENT OF *PSEUDOFOLLICULITIS BARBAE***

[76] Inventor: Michael J. Burns, 2935 Cornell St., Paducah, Ky. 42003

[21] Appl. No.: 193,435

[22] Filed: Feb. 8, 1994

[51] Int. Cl.⁶ .................. A61K 7/13; A61K 35/78; A61K 33/40; A61K 31/125

[52] U.S. Cl. .................. 424/73; 424/195.1; 424/401; 424/DIG. 5; 514/714; 514/828; 514/844; 514/848; 514/859; 514/861; 514/880; 514/886; 514/944; 514/969; 514/675; 514/692

[58] Field of Search .............. 424/73, 195.1, DIG. 5, 424/401; 514/692, 714, 828, 844, 848, 859, 861, 880, 886, 944, 969

[56] References Cited

U.S. PATENT DOCUMENTS

| | | | |
|---|---|---|---|
| 4,075,353 | 2/1978 | Mandy et al. | 424/338 |
| 4,163,800 | 8/1979 | Wickett et al. | 424/326 |
| 4,228,163 | 10/1980 | Bliss | 424/240 |
| 4,384,589 | 5/1983 | Morris | 132/88.5 |
| 4,443,437 | 4/1984 | Prokosch et al. | 424/195.1 |
| 4,463,016 | 7/1984 | Burgess | 424/347 |
| 4,525,344 | 6/1985 | Tutsky | 424/73 |
| 4,585,650 | 4/1986 | Newberry et al. | 424/73 |
| 4,593,046 | 6/1986 | Gruber | 514/717 |
| 4,627,934 | 12/1986 | Lindaver et al. | 424/195.1 |
| 4,775,530 | 10/1988 | Perricone | 424/73 |
| 4,810,496 | 3/1989 | Jensen | 424/127 |
| 4,867,967 | 9/1989 | Crutcher | 424/73 |
| 4,923,900 | 5/1990 | De Villez | 514/714 |
| 4,980,159 | 12/1990 | Koslo | 424/73 |
| 4,994,265 | 2/1991 | White | 424/73 |
| 5,034,221 | 7/1991 | Rosen et al. | 424/73 |
| 5,043,356 | 8/1991 | Fulton | 514/549 |
| 5,204,093 | 4/1993 | Victor | 424/73 |
| 5,252,331 | 10/1993 | Curtis et al. | 424/73 |
| 5,279,837 | 1/1994 | Hill | 424/182 |
| 5,340,571 | 8/1994 | Grace | 424/73 |

*Primary Examiner*—Shep K. Rose
*Attorney, Agent, or Firm*—Famiglio & Massinger

[57] ABSTRACT

A topical agent and method for the treatment and prevention of pseudofolliculitis barbae, related secondary bacterial infections and other skin conditions associated with shaving result from a combination of three ingredients, namely benzoyl peroxide, camphor oil and aloe vera present in 15:4:1 parts by volume of the composition, respectively.

9 Claims, No Drawings

TOPICAL AGENT AND METHOD FOR THE TREATMENT OF *PSEUDOFOLLICULITIS BARBAE*

BACKGROUND OF THE INVENTION

1. Field of the Invention

The subject invention is directed to a topical agent for the treatment and prevention of pseudofolliculitis barbae. More particularly, the subject invention is directed to a topical agent comprising benzoyl peroxide, camphor oil and aloe vera.

2. Brief Description of the Prior Art

More commonly known as "razor bumps", pseudofolliculitis barbae is a skin condition clinically characterized by papules and papulopustules of the epidermis resulting from the ingrowth of strongly curved facial hairs at a location closely proximate the follicle from which they emerged. This antigenic, foreign-body reaction may be further augmented by secondary infection caused by bacteria, such as staphylococcus aureaus, and other gram positive organisms.

Pseudofolliculitis barbae most commonly affects the neck and jowls of men black in particular, who shave. Hairs that are strongly curved and that emerge closely parallel to the skin are biased toward reentry into the skin because, during shaving, they are cut at oblique angles forming relatively sharp pointed tips capable of skin penetration as the hair grows. Existing skin elevations (bumps) are often cut while shaving, an occurrence which is not only painful, but serves to exacerbate infection.

Heretofore, attempts to treat this condition have not been without significant shortcomings. Abstinence from shaving has been recommended in combination with various therapeutic agents and antibiotics; the former permits growth of the hair until its sharpened tip springs from the skin, the latter remedies existing lesions and infection. Obviously, however, total abstinence from shaving is impractical for most professionals and others who prefer a clean shaven appearance.

The use of chemical depilatory compositions have also been suggested for the removal of hairs before they can reenter the skin. Such compounds, however, are considered by some to be too time consuming to apply and too harsh and irritating to the skin.

Additionally, U.S. Pat. No. 4,867,967 issued Sep. 19, 1989 to Crutcher discloses the use of topical or low-dose systemic antibiotics for the amelioration of pseudofolliculitis barbae by limiting the inflammatory process until such time that the inciting hair can be freed. Disadvantages associated with this form of treatment include relatively high costs associated with prescription refills and that such drugs are often too strong for consumers with only mild cases. The Crutcher patent itself is one of many cases teaching the use of various compounds or unique combinations thereof for treatment and/or prevention of the condition. Topical application of povidone-iodine (Crutcher), 4-chloro-3,5-diloweralkyl-phenol (U.S. Pat. No. 4,463,016), alpha hydroxy acids and derivatives (U.S. Pat. No. 4,775,530) and acetylsalicylic acid together with isopropyl alcohol (U.S. Pat. No. 5,034,221) are illustrative. None of these references teach the use of benzoyl peroxide together with camphor oil and aloe vera, and publication of data in support of their efficacy for the treatment of pseudofolliculitis barbae is not readily available.

An earlier reference, U.S. Pat. No. 4,228,163 issued Oct. 14, 1980 to Bliss, teaches the combination of benzoyl peroxide and chlorohydroxyquinoline as a topical preparation for the treatment of razor bumps. The latter of these two compounds possesses anti-bacterial and anti-fungal activity. The former, benzoyl peroxide, is a colorless, odorless, tasteless crystalline solid having the chemical structural formula:

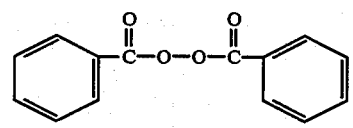

With regard to its method of action, benzoyl peroxide is an antibacterial, mildly comedolytic, and sebostatic agent. It exerts its antimicrobial action in the follicles and possesses bactericidal action against Propionbacterium acnes and Staphylococcus epidermidis. This activity is presumed due to release of active or free-radical oxygen capable of oxidizing bacterial proteins since resolution of acne coincides with reduction in Propionbacterium acnes and of free fatty acids on the surface of the skin.

Benzoyl peroxide is most commonly used in concentrations of 2.5% to 10% and may be used alone in mild to moderate acne, or as an adjunct in acne treatment regimens. In these respects, attention is particularly invited to U.S. Pat. Nos. 3,535,422 and 3,530,217, for example. Benzoyl peroxide also has wound healing characteristics which may be attributed to bactericidal or microbicidal action, granulation stimulation and hyperbaric oxygenation.

According to Bliss, benzoyl peroxide, in combination with chlorohydroxyquinoline, is effective for the treatment of pseudofolliculitis barbae. In accordance with the treatment method of Bliss, however, benzoyl peroxide must be admixed with a composition containing the chlorohydroxyquinoline shortly before its topical application to the infected area, presumably because its efficacy is diminished shortly thereafter. The limited shelf life of this synergistic compound and the consequent requirement of mixing just prior to use is considered by some to be laborious and unappealing. Nevertheless, the use of benzoyl peroxide as an important constituent of a pseudofolliculitis treatment regimen cannot be ignored.

More particularly, it has been discovered that the combination of benzoyl peroxide, camphor oil and aloe vera in specific proportions produces an overwhelmingly effective therapeutic and preventative agent for the treatment of pseudofolliculitis barbae. The efficacy of this composition does not require the presence or expense of chlorohydroxyquinoline, nor does it require the mixing of its constituent ingredients immediately prior to application to the effected area. The composition does, however, require the presence of the aforementioned camphor oil and aloe vera ingredients to function within the contemplation of this invention. Neither of these ingredients have heretofore been combined with benzoyl peroxide as herein described.

SUMMARY OF THE INVENTION

The subject invention more specifically relates to a topical agent and method for the treatment and prevention of pseudofolliculitis barbae through the application of a combination of benzoyl peroxide, camphor oil and aloe vera to the neck, face or other effected skin surface.

The ingredients in this composition are present, for example, in 15:4:1 parts by volume, respectively, and have a synergistic effect capable of affording therapeutic relief from pseudofolliculitis barbae and associated skin conditions and secondary bacterial infections.

It is, therefore, a primary object of the subject invention to provide a novel topical agent and method for both the treatment and prevention of pseudofolliculitis barbae and related secondary bacterial infections.

It is also a primary object of the subject invention to provide a topical agent for the treatment of pseudofolliculitis barbae which may be employed without the occurrence of skin irritation or other more serious side effects.

It is also an object of the present invention to provide a topical agent for the treatment of pseudofolliculitis barbae which has a suitable shelf life and does not require mixing of its constituent ingredients by the user.

It is another object of the present invention to provide a topical agent for the treatment and prevention of other skin irritations associated with shaving such as razor burn.

Other objects and advantages of the present invention will be apparent upon reference to the accompanying description when taken in conjunction with the following drawings.

DETAILED DESCRIPTION OF THE PREFERRED EMBODIMENT

The subject topical agent and method for the treatment and prevention of pseudofolliculitis barbae, related secondary bacterial infections and other skin conditions associated with shaving result from a combination of three ingredients, namely benzoyl peroxide, camphor oil and aloe vera. It has been surprisingly discovered herein that this novel combination of ingredients is an overwhelmingly effective therapeutic agent for the treatment of these conditions and particularly of inflammation and infection.

The above combination of ingredients, when expressed as percentages by volume, are preferably related as follows:

| | |
|---|---|
| benzoyl peroxide (10%) | 75% |
| camphor | 05% |
| aloe vera (pure) | 20% |

The primary ingredient, benzoyl peroxide, is incorporated in a suitable carrier, not chemically reactive with benzoyl peroxide at ambient temperature and pressure, to form a 10% concentrate of the active. Benzoyl peroxide of this concentration comprises between 70 to 80% by volume of the total formulation.

With regard to the inert carrier, various lower alcohols may be employed such as ethanol or isopropanol which further serve to dissolve aliphats in the skin which would otherwise block the active ingredients from contact with the effected follicles, thereby diminishing the efficacy of the therapeutic. Alternatively, the benzoyl peroxide may be admixed with those dry non-liquid crystalline carriers disclosed in Bliss ('163) including calcium phosphate: talc, diatomaceous earth, calcium silicate, starch and polyhydric alcohols such as dextrin and dextran.

The second ingredient, camphor, has been used for many centuries as an antipruritic and topical rubefacient, abortifacient, aphrodisiac, contraceptive, cold remedy, suppressor of lactation and antiseptic. Camphor is a cyclic ketone of the hydroaromatic terpene group, with a penetrating characteristic odor and a pungent, aromatic taste. A tough, gummy crystalline compound having the molecular formula $C_{10}H_{16}O$, camphor is currently produced synthetically and sold over-the-counter in concentrations of from below 1% to above 10%. Camphor in liquid form is rapidly absorbed through the skin. Camphorated oil, for instance, typically contains approximately 20% camphor while camphor spirits typically contain approximately 10% camphor. Both are commonly employed as mild external analgesics.

The third ingredient, aloe vera, is a native Mediterranean plant that has been used for centuries in folk medicine for the treatment of burns and skin injuries. Of the more than 300 species of aloes, only a few have been used medicinally. The latex is the plant portion most commonly used by the pharmaceutical industry. The aloe gel, which is derived from the thin-walled mucilaginous cells of the plant, more often is used by the cosmetic industry. The topical use of aloe extracts is approved for use on abrasions, burns, and insect bites. Aloe extracts have good emollient and moisturizing properties. In addition, they exhibit bradykinase activity, and this may provide pharmacological support for its anti-inflammatory properties in the subject topical agent for treatment of pseudofolliculitis barbae.

In addition to its anti-inflammatory, emollient and moisturizing properties, aloe vera further serves to provide the desired consistency of the subject invention as measured by its ability to applied smoothly and evenly to the skin. Moreover, because aloe vera is a non-oil based organic derivative, it will not interfere with the ability of benzoyl peroxide or camphor to contact the affected skin surface.

Together, the three primary ingredients of the subject invention may be combined with other well known chemical expedients to form any of the group consisting of a gel, shaving lotion, shaving foam, aftershave, soap, ointment, lotion or stick. In any case, however, the ratio of primary ingredients remains the same and comprises 45:25:1 of benzoyl peroxide, camphor and aloe vera, respectively. Each of said ingredients are simply mixed together to a homogenous state. The following example is illustrative of a formulation of the present invention and its method of use, but is not intended to limit its scope as claimed.

EXAMPLE 1

Benzoyl peroxide (10%) having a measured volume of 30 cc is charged to a mixing vessel followed by addition of 8 cc aloe vera gel (100%) and 2 cc camphor oil and the ingredients mixed to a homogenous state at ambient temperature. Immediately after shaving, a small amount of the topical agent is applied with the fingertip to the shaven areas until no longer visible in a massaging-like manner covering the entire area shaved. For more serious cases of pseudofolliculitis barbae, application may be repeated preferably at bed time.

For best results, skin areas to be treated should be rinsed thoroughly prior to administration; washing the face once or twice daily. Controlling the amount of drying or peeling of the skin may be accomplished by modifying application frequency or concentration. For treatment with other dose forms: cleanse skin, then smooth a small amount over affected area; apply once daily for first few days; if redness, dryness, or peeling does not occur in 3 days, increase application to twice daily; reduce dosage if bothersome peeling or dryness occurs.

Although the present invention has been described with reference to the particular embodiments herein set forth, it is understood that the present disclosure has been made only by way of example and that numerous changes in details of construction may be resorted to without departing from the spirit and scope of the invention. Thus, the scope of the invention should not be limited by the foregoing specifications, but rather only by the scope of the claims appended hereto.

What is claimed is:

1. A composition for topical treatment of pseudofolluculitis barbae, consisting essentially of the following ingredients by volume:
   a. benzoyl peroxide—75%
   b. aloe vera gel—20%; and
   c. camphor oil—5%.

2. A topical agent for the treatment and prevention of pseudofolliculitis barbae consisting essentially of:
   a. approximately 75% by volume of 10% benzoyl peroxide;
   b. approximately 20% by volume of aloe vera combined and thoroughly mixed with said benzoyl peroxide; and
   c. approximately 5% by volume of camphor oil thoroughly mixed with said benzoyl peroxide and said aloe vera.

3. A process for producing a composition in accordance with claim 2 for treatment and prevention of pseudofolliculitis barbae comprising:
   a. mixing approximately 75% by volume of benzoyl peroxide (10%) with approximately 20% by volume of aloe vera and approximately 5% by volume of camphor oil until a homogenous state is achieved.

4. The topical agent of claim 2, wherein said aloe vera comprises pure aloe vera gel.

5. The topical agent of claim 1, wherein said benzoyl peroxide has a concentration of 10%.

6. The topical agent of claim 2, wherein said camphor oil contains between 10–20% camphor.

7. The topical agent of claim 2, wherein said benzoyl peroxide, aloe vera and camphor oil comprise components of a topical preparation selected from the group consisting of a gel, shaving cream, shaving foam, after shave, soap, ointment, lotion and stick.

8. A method for treating pseudofolliculitis barbae which comprises applying to the affected area of the skin and effective amount of the topical agent according to claim 2.

9. A method for treating pseudofolliculitis barbae in humans and the prophylactic treatment thereof, which comprises: topically applying to involved areas of the human body an effective amount of a composition in accordance with claim 2.

* * * * *